(12) United States Patent
Weber et al.

(10) Patent No.: US 11,100,665 B2
(45) Date of Patent: Aug. 24, 2021

(54) ANATOMICAL MEASUREMENTS FROM ULTRASOUND DATA

(71) Applicant: KONINKLIJKE PHILIPS N.V., Eindhoven (NL)

(72) Inventors: Frank Michael Weber, Hamburg (DE); Irina Waechter-Stehle, Hamburg (DE); Christian Buerger, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 82 days.

(21) Appl. No.: 16/493,386

(22) PCT Filed: Mar. 5, 2018

(86) PCT No.: PCT/EP2018/055274
§ 371 (c)(1),
(2) Date: Sep. 12, 2019

(87) PCT Pub. No.: WO2018/166824
PCT Pub. Date: Sep. 20, 2018

(65) Prior Publication Data
US 2020/0074664 A1 Mar. 5, 2020

(30) Foreign Application Priority Data
Mar. 13, 2017 (EP) .................................. 17160479

(51) Int. Cl.
*G06T 7/62* (2017.01)
*G06T 7/149* (2017.01)
(Continued)

(52) U.S. Cl.
CPC .............. *G06T 7/62* (2017.01); *A61B 8/5223* (2013.01); *G06T 7/149* (2017.01); *G06T 17/00* (2013.01);
(Continued)

(58) Field of Classification Search
CPC ..... G06T 7/0012; G06T 7/11; G06T 7/60–68; G06T 7/149; G06T 7/174; G06T 17/00;
(Continued)

(56) References Cited

U.S. PATENT DOCUMENTS

| 6,346,124 B1 * | 2/2002 | Geiser | G06T 7/0012 |
| | | | 600/450 |
| 2003/0160786 A1 * | 8/2003 | Johnson | G06T 17/20 |
| | | | 345/419 |

(Continued)

OTHER PUBLICATIONS

International Search Report and Written Opinion for International Application No. PCT/EP2018/055274, filed Mar. 5, 2018, 17 pages.
(Continued)

*Primary Examiner* — Vu Le
*Assistant Examiner* — Julius Chenjun Chai (57) ABSTRACT

The application discloses a computer-implemented method (100) of providing a model for estimating an anatomical body measurement value from at least one 2-D ultrasound image including a contour of the anatomical body, the method comprising providing (110) a set of 3-D ultrasound images of the anatomical body; and, for each of said 3-D images, determining (120) a ground truth value of the anatomical body measurement; generating (130) a set of 2-D ultrasound image planes each including a contour of the anatomical body, and for each of the 2-D ultrasound image planes, extrapolating (140) a value of the anatomical body measurement from at least one of an outline contour measurement and a cross-sectional measurement of the anatomical body in the 2-D ultrasound image plane; and generating (150) said model by training a machine-learning algorithm to generate an estimator function of the anatomical body measurement value from at least one of a determined outline contour measurement and a determined cross-sectional measurement of a contour of the anatomical body within a 2-D
(Continued)

ultrasound image using the obtained ground truth values, extrapolated values and at least one of the outline contour measurements and the cross-sectional measurements as inputs of said machine-learning algorithm. A computer-implemented method of deploying such a model, a computer program product, an ultrasound image processing apparatus and an ultrasound imaging system adapted to implement such methods are also disclosed.

12 Claims, 5 Drawing Sheets

(51) Int. Cl.
*A61B 8/08* (2006.01)
*G06T 17/00* (2006.01)

(52) U.S. Cl.
CPC ............... *G06T 2207/10136* (2013.01); *G06T 2207/20081* (2013.01); *G06T 2207/30048* (2013.01)

(58) Field of Classification Search
CPC . G06T 2207/10132; G06T 2207/10136; G06T 2207/20081; G06T 2207/30048; A61B 8/52–5223; A61B 34/10
See application file for complete search history.

(56) References Cited

U.S. PATENT DOCUMENTS

| | | |
|---|---|---|
| 2011/0201935 A1* | 8/2011 | Collet-Billon ...... G01S 15/8993 600/443 |
| 2014/0328527 A1 | 11/2014 | Zhou et al. |
| 2015/0112182 A1* | 4/2015 | Sharma ................ A61B 5/7282 600/408 |
| 2015/0272541 A1 | 10/2015 | Hyuga |
| 2016/0081663 A1* | 3/2016 | Chen .................... A61B 8/0866 600/425 |
| 2016/0300120 A1* | 10/2016 | Haas ..................... G06K 9/6206 |
| 2018/0042578 A1* | 2/2018 | Anand ................ A61B 8/5215 |
| 2019/0000424 A1* | 1/2019 | Samset ................ A61B 8/0808 |

OTHER PUBLICATIONS

Schlett, et al., "Simple Area-based Measurement for Multidetector Computed Tomography to predict Left Ventricular Size", Eur Radiol. Jul. 2010; 20(7): pp. 1-14.

Ecabert, Olivier, et al. "Automatic model-based segmentation of the heart in CT images." Medical Imaging, IEEE Transactions on, vol. 27, Issue 9 (2008): 1189-1201. (Abstract).

* cited by examiner

ANATOMICAL MEASUREMENTS FROM ULTRASOUND DATA

RELATED APPLICATIONS

This application is the U.S. National Phase application under 35 U.S.C. § 371 of International Application No. PCT/EP2018/055274, filed on Mar. 5, 2018, which claims the benefit of European Application No. 17160479.6, filed Mar. 13, 2017. These applications are hereby incorporated by reference herein.

FIELD OF THE INVENTION

The present invention relates to a computer-implemented method of providing a model for estimating an anatomical body measurement value from at least one 2-D ultrasound image including a contour of the anatomical body.

The present invention further relates to a computer-implemented method of estimating an anatomical body measurement value from at least one 2-D ultrasound image including a contour of the anatomical body with such a model.

The present invention further relates to a computer program product for implementing such methods on an ultrasound image processing apparatus.

The present invention further relates to an ultrasound image processing apparatus implementing such methods.

The present invention further relates to an ultrasound imaging system comprising such an ultrasound image processing apparatus.

BACKGROUND OF THE INVENTION

Ultrasound plays an essential role in many diagnostic imaging techniques including but not limited to cardiovascular imaging. In this context, diagnosis and treatment planning typically rely on a clear delineation of relevant anatomical sites such as the ventricles, the atria or surrounding vessels in the cardiac ultrasound images in order to facilitate meaningful evaluation of the heart under investigation. The same principle applies to other anatomical bodies within a patient under investigation, such as other (parts of) organs, a foetus in pregnant female patient, and so on.

Accurate measurements (e.g. of the volume) of such anatomical bodies, e.g. cardiac chambers, such as the left ventricle, can be generated from 3-D ultrasound images using anatomically intelligent model-based segmentation, where generic, shape-constrained anatomical body models, e.g. heart models, are fitted to the imaging data. For example, model-based segmentation for 3-D ultrasound images is disclosed in US 2011/0201935A, and a heart model is disclosed in WO 2016/142204 A1. The heart model may be subsequently used as an aid to subject the mapped cardiac structure in the ultrasound imagery to segmentation algorithms in order to obtain the dimensions of interest of the cardiac anatomical sites under investigation, e.g. by mapping such a model onto a volumetric image. A suitable segmentation algorithm is disclosed by O. Ecabert et al. in "Automatic Model-Based Segmentation of the Heart in CT Images", IEEE Transactions on Medical Imaging, 2008 (27), pages 1189-1201.

Despite the availability of such anatomically intelligent model-based segmentation tools, many operators of ultrasound systems, e.g. clinicians, still rely on 2-D ultrasound images to estimate 3-D anatomical measurements, such as volumes of the anatomical bodies under investigations, using geometrical assumptions. There may be many reasons for this. For example, an operator may be unfamiliar or lack confidence in interpreting 3-D ultrasound images and therefore prefer to rely on 2-D ultrasound images, e.g. 2-D image slices of a 3-D ultrasound image or a sequence of 2-D ultrasound images, to obtain such anatomical measurements. Or, the operator may not have access to 3-D ultrasound image data, in which case the operator needs to rely on 2-D ultrasound images to obtain the desired anatomical measurement. In yet another scenario, the acquisition of 3-D ultrasound images may be practically unfeasible, for example in the field of contrast imaging, where the acquisition frame rate may be insufficient to capture useful 3-D volumes. This for example can be a real issue in echocardiography techniques such as TTE and TEE imaging.

CHRISTOPHER L. SCHLETT ET AL.: "Simple area-based measurement for multidetector computed tomography to predict left ventricular size", EUROPEAN RADIOLOGY, vol. 20, no. 7, 4 Mar. 2010 (Mar. 4, 2010), pages 1590-1596, XP055384783, DE discloses a comparison, using simple linear regression analysis to determine correlation, of actual measurements of ventricular size with those estimated using 2D CT image slices by automatically detecting border contours in each image and manually adjusting them where necessary, then using a formula to calculate the ventricular size.

However, such 3-D anatomical measurements derived from 2-D ultrasound images tend to be unreliable and prone to errors, in particular where incorrect geometrical assumptions are made or where the 2-D ultrasound image does not provide an optimal view of the anatomical body of interest.

SUMMARY OF THE INVENTION

The present invention seeks to provide a computer-implemented method of developing a model that receives one or more 2-D ultrasound images including a contour of anatomical body of interest as an input and produces an estimate of a 3-D anatomical body measurement value from such an input.

The present invention further seeks to provide a computer-implemented method of using such a model to provide an estimate of a 3-D anatomical body measurement value from one or more 2-D ultrasound images including a contour of the anatomical body of interest.

The present invention further seeks to provide a computer program product for implementing such methods on an ultrasound image processing apparatus.

The present invention further seeks to provide an ultrasound image processing apparatus adapted to implement such methods.

The present invention further seeks to provide an ultrasound imaging system including such an ultrasound image processing apparatus.

The invention is defined by the claims.

According to an aspect, there is provided a computer-implemented method of generating a model for estimating an anatomical body measurement value from at least one 2-D ultrasound image including a contour of the anatomical body, the method comprising:

providing a set of 3-D ultrasound images of the anatomical body;

for each of said 3-D ultrasound images, determining a ground truth value of the anatomical body measurement, for example by manual measurement of the value or by mapping a segmentation model onto the 3-D image;

generating from the set of 3-D images a set of 2-D ultrasound image planes each including a contour of the anatomical body and, for each of the 2-D ultrasound image planes, estimating a value of the anatomical body measurement from at least one of an outline contour measurement and a cross-sectional measurement of the anatomical body in the 2-D ultrasound image plane; and generating said model by training a machine-learning algorithm so that it will generate an estimate of the anatomical body measurement value from inputs comprising at least one of an outline contour measurement and a cross-sectional measurement of a contour of the anatomical body that are determined by a user from a 2-D ultrasound image, the training being done by inputting to the machine-learning algorithm the ground truth values, the corresponding estimated values and at least one of the corresponding outline contour measurements and the corresponding cross-sectional measurements.

In accordance with the present invention, such a model is developed using ground truth 3-D anatomical measurement values of the anatomical body of interest as derived from 3-D ultrasound images of the anatomical body to train a machine learning algorithm using a set of 2-D ultrasound images including a contour of the anatomical body to relate contour-related measurements such as contour outline measurements and contour cross-sectional measurements, e.g. diameter or area measurements of the cross-section of the anatomical body into 2-D ultrasound images such that the machine learning algorithm can predict the 3-D anatomical measurement values from the contour-related measurements of a 2-D ultrasound image it receives as an input. In this manner, a user of the model can obtain an estimate of the 3-D anatomical measurement value of interest based on a learned relationship (function) between the contour-related measurements of that particular 2-D ultrasound image with the ground truth data as developed with the machine learning algorithm, such that the user does not have to rely on geometric assumptions to obtain the 3-D anatomical measurement value of interest, thus reducing the risk of the obtained measurement value being erroneous.

In an embodiment, providing the set of 2-D ultrasound image planes comprises generating the 2-D ultrasound image planes from the set of 3-D ultrasound images.

This obviates the need to provide separate 2-D ultrasound images for the training purpose of the machine learning algorithm and has the further advantage that typical slicing directions of the 3-D ultrasound images, e.g. 2-chamber view and 4-chamber view directions in case of echocardiography images, can be easily obtained, which may be used to strengthen the reliability of the correlation function developed by the machine learning algorithm for such commonly used views. Hence, in an example embodiment, providing a set of 2-D image planes comprises providing a first set of 2-D image planes providing a 2-chamber view of a human heart and a second set of 2-D image planes providing a 4-chamber view of the human heart.

Preferably, the computer-implemented method further comprises training the machine-learning algorithm to generate a further estimator function to estimate an uncertainty in the estimated anatomical body measurement value using the obtained ground truth values, extrapolated values and at least one of the outline contour measurements and the cross-sectional measurements as inputs of said machine-learning algorithm. It is particularly useful to provide an indication of the uncertainty in the 3-D anatomical body measurement value obtained with a model, such that a user of the model can determine if the obtained value can be relied upon. This furthermore may provide the user with an indication of whether the 2-D ultrasound image acquisition should be repeated along a different viewing angle, e.g. a different scanning direction, in order to reduce the uncertainty in the 3-D anatomical body measurement value obtained with the model, as a high uncertainty may be an indication of a non-optimal view, e.g. a distorted view, of the anatomical body of interest in the 2-D ultrasound images under investigation, such that the desired 3-D anatomical body measurement value cannot be reliably extrapolated from such images.

In an embodiment, determining a ground truth value of the anatomical body measurement comprises mapping a segmentation model for identifying the anatomical body to said anatomical body within the 3-D ultrasound image; and deriving the ground truth value of the anatomical body measurement from the mapped segmentation model. In this manner, an accurate determination of the 3-D anatomical body measurement value can be obtained in a straightforward manner. This may further involve user-operated adjustment of the mapping of the segmentation model onto the anatomical body within the 3-D ultrasound image to further improve this accuracy. The ground truth value then may be obtained e.g. from a 3-D mesh of the volume delimited by the segmentation model.

Such a segmentation model advantageously may be further used to calculate the set of 2-D image planes from the mapping of the segmentation model to the anatomical body within the 3-D ultrasound image, thereby providing a straightforward manner of generating the 2-D ultrasound image planes.

In a preferred embodiment, the anatomical body is a human heart and the segmentation model is a heart model although segmentation models for different anatomical bodies, e.g. different organs or foetuses may also be used.

Preferably, providing a set of 2-D ultrasound image planes comprises providing a plurality of subsets of 2-D ultrasound image planes, wherein the 2-D ultrasound image planes in each subset are under a defined angle with a defined axis of the 3-D ultrasound images, said defined angles differing between subsets. In this manner, the machine learning algorithm can reliably develop the correlation function between a cross-sectional view of the anatomical body of interest in a 2-D ultrasound image and the 3-D anatomical measurement value of the anatomical body of interest for a large number of 2-D ultrasound image views, i.e. under a large number of viewing angles, thereby improving the robustness of the developed model.

According to another aspect, there is provided a computer-implemented method of estimating an anatomical body measurement value, from at least one 2-D ultrasound image including a contour of the anatomical body, using the model described above for estimating an anatomical body measurement value from at least one 2-D ultrasound image, comprising:

providing the at least one 2-D ultrasound image including a contour of the anatomical body;

determining at least one of an outline contour measurement and a cross-sectional measurement of the anatomical body from the at least one 2-D ultrasound image;

feeding the determined outline contour measurement and/or the determined cross-sectional measurement as inputs into said model; and receiving an estimated anatomical body measurement value from the model in response to said inputs.

In a preferred embodiment, the computer-implemented method further comprises receiving an estimated uncertainty of the estimated anatomical body measurement value from the model in response to said inputs. This allows its user to ascertain the reliability of the anatomical body measurement value provided by the model, such that for example in case of unreliable measurement values, e.g. values having a large estimated uncertainty, the user may decide to either obtain the measurement value in another way or acquire a new set of 2-D ultrasound images, e.g. along a different viewing angle, in order to reduce this uncertainty and improve the reliability of the estimated anatomical body measurement value, e.g. by basing the measurement value on a combination of the original set and the new set of 2-D ultrasound images.

In a further advantageous embodiment, the computer-implemented method further comprises identifying a plane orientation relative to the anatomical body for which said estimated uncertainty is minimized and communicating said plane orientation to a user or to an ultrasound probe. Such plane orientation information can be utilized by the user to manually acquire a new set of 2-D ultrasound images in accordance with the plane orientation information from which a reliable estimate of the anatomical body measurement value of interest can be obtained or alternatively such plane orientation information may be leveraged by a mechanically or electronically steered probe to obtain such 2-D ultrasound images in accordance with the plane orientation information in an automated manner.

In an example embodiment, the anatomical body is the human heart and the measurement value of interest may be a volume of the heart or of a chamber of the heart. In such an embodiment, providing the at least one 2-D ultrasound image including a contour of the anatomical body may further comprise providing a first 2-D ultrasound image including a contour of the human heart at a first point of a cardiac cycle; providing a second 2-D ultrasound image including a contour of the human heart at a second point of a cardiac cycle; and deriving an estimation of an ejection fraction of the human heart from a difference between the estimated volume for the first 2-D ultrasound image and the estimated volume for the second 2-D ultrasound image.

According to another aspect, there is provided a computer program product comprising a computer readable storage medium having computer readable program instructions embodied therewith for, when executed on a processor arrangement of an ultrasound image processing apparatus, cause the processor arrangement to implement the method of any of the herein described embodiments. Such a computer program product therefore may be used to configure the ultrasound image processing apparatus to develop and/or implement the model for estimating the 3-D anatomical body measurement value of interest from one or more 2-D ultrasound images obtained by the ultrasound image processing apparatus, e.g. from an ultrasound probe from a data storage arrangement in which such images are stored.

According to another aspect, there is provided an ultrasound image processing apparatus comprising a processor arrangement and the aforementioned computer program product, wherein the processor arrangement is adapted to execute said computer readable program instructions. Such an ultrasound image processing apparatus therefore is configured to develop and/or implement the model for estimating the 3-D anatomical body measurement value of interest from one or more 2-D ultrasound images obtained by the ultrasound image processing apparatus, e.g. from an ultrasound probe from a data storage arrangement in which such images are stored. Consequently, such an ultrasound image processing apparatus may be advantageously used to reliably obtain estimates of the 3-D anatomical body measurement value of interest from such 2-D ultrasound images without its user having to provide geometrical assumptions about the relationship between the 2-D ultrasound images and the anatomical body of interest, thereby reducing the risk of the user obtaining erroneous measurement values of features of interest of such an anatomical body.

According to another aspect, there is provided an ultrasound imaging system comprising the aforementioned ultrasound image processing apparatus and an ultrasound imaging probe for providing the ultrasound image processing apparatus with the at least one 2-D ultrasound image. Such an ultrasound imaging system may be used to reliably generate estimates of a measurement value of an anatomical body of interest in 2-D ultrasound images captured with the ultrasound imaging probe. For example, the ultrasound imaging probe may be an echocardiography probe adapted to capture ultrasound images of a heart such as a human heart.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

It should be understood that the Figures are merely schematic and are not drawn to scale. It should also be understood that the same reference numerals are used throughout the Figures to indicate the same or similar parts.

Figure 1:
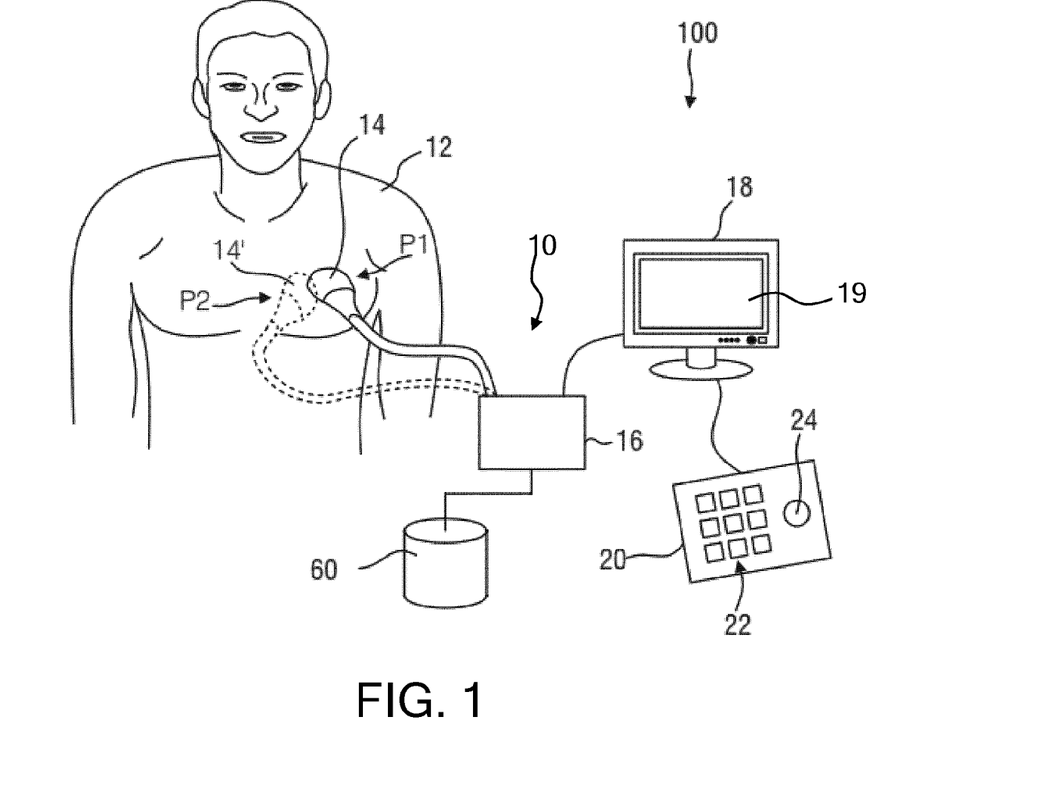
FIG. 1 schematically depicts an ultrasound imaging system according to an embodiment.

In the present application, where reference is made to a set of ultrasound images, it should be understood that such a set contains at least one ultrasound image. FIG. 1 shows a schematic illustration of an ultrasound system 100, in particular a medical two-dimensional (2-D) or three-dimensional (3-D) ultrasound imaging system. The ultrasound system 100 may be applied to inspect a volume of an anatomical site, in particular an anatomical site of a patient 12, such as the patient's heart. This for example may involve monitoring the anatomical site over a period of time to track progress of a condition affecting the anatomical site. The ultrasound system 100 comprises an ultrasound probe 14 having at least one transducer array having a multitude of transducer elements for transmitting and/or receiving ultrasound waves. In one example, each of the transducer elements can transmit ultrasound waves in form of at least one transmit impulse of a specific pulse duration, in particular a plurality of subsequent transmit pulses. Such an ultrasound probe 14 may be a probe to be applied to a skin portion, e.g. in the chest region, of the patient 12. In some embodiments, the probe 14 may be a transesophageal echocardiography (TEE) probe or a transthoracic echocardiography (TTE) probe.

The transducer elements may be arranged in a one-dimensional array, e.g. in case of 2-D medical imaging, or in a two-dimensional array, in particular for providing a multi-planar or three-dimensional image in case of a 3-D ultrasound system 100. A particular example for a three-dimensional ultrasound system which may be the CX40 Compact Xtreme ultrasound system sold by the applicant, in particular together with a X6-1 or X7-2t TEE transducer of the applicant or another transducer using the xMatrix technology of the applicant. In general, matrix transducer systems as found on Philips iE33 systems or mechanical 3D/4D transducer technology as found, for example, on the Philips iU22 and HD15 systems may be applied in conjunction with the current invention.

The ultrasound probe 14 is typically communicatively coupled to an ultrasound image processing apparatus 10, which coupling may be achieved in any suitable manner, e.g. a wireless coupling or a wired coupling such as through a coaxial cable, through which control instructions for the ultrasound probe 14 may be provided by the ultrasound image processing apparatus 10. Such an ultrasound image processing apparatus 10 may take any suitable shape, such as a dedicated workstation or console of the ultrasound imaging system 100 or alternatively may be a general-purpose computing device, e.g. a personal computer, laptop computer or tablet computer on which a computer program product is installed that configures the computing device to be operable as the ultrasound image processing apparatus 10.

The ultrasound image processing apparatus 10 may comprise a processor arrangement 16 including an image reconstruction unit that controls the provision of a 2-D or 3-D image sequence via the ultrasound system 100. As will be explained in further detail below, the image reconstruction unit may control not only the acquisition of data via the transducer array of the ultrasound probe 14, but also signal and image processing that form the 2-D or 3-D image sequence out of the echoes of the ultrasound beams received by the transducer array of the ultrasound probe 14.

The ultrasound system 100 may further comprise a display device 18 (from here on also referred to as display 18) for displaying the 2-D or 3-D image or image sequence to the user. The display 18 may form an integral part of or may be communicatively coupled to the ultrasound image processing apparatus 10. The display 18 may comprise a touchscreen 19 through which a user may interact with image data displayed thereon, e.g. displayed 2-D images, 2-D slices of a 3-D volumetric ultrasound image, or a volume rendered display image of the volumetric ultrasound image of an anatomical region of interest of the patient 12, such as the patient's heart in some embodiments of the present invention, as will be explained in further detail below. Any suitable type of touchscreen 19 may be used in the display 18. Still further, an input device 20 may be provided that may comprise a user interface 22 such as a keyboard and further inputting devices, for example a trackball 24. The input device 20 might be connected to the display 18 or directly to the image reconstruction unit 16. The ultrasound system 100 may further comprise a data storage arrangement 60, e.g. one or more memory devices, hard disks, optical discs, or the like, in which the processor arrangement or image reconstruction unit 16 may store image frames and image frame processing data, e.g. for evaluation at a later date, i.e. upon completion of the ultrasound image data acquisition.

Figure 2:
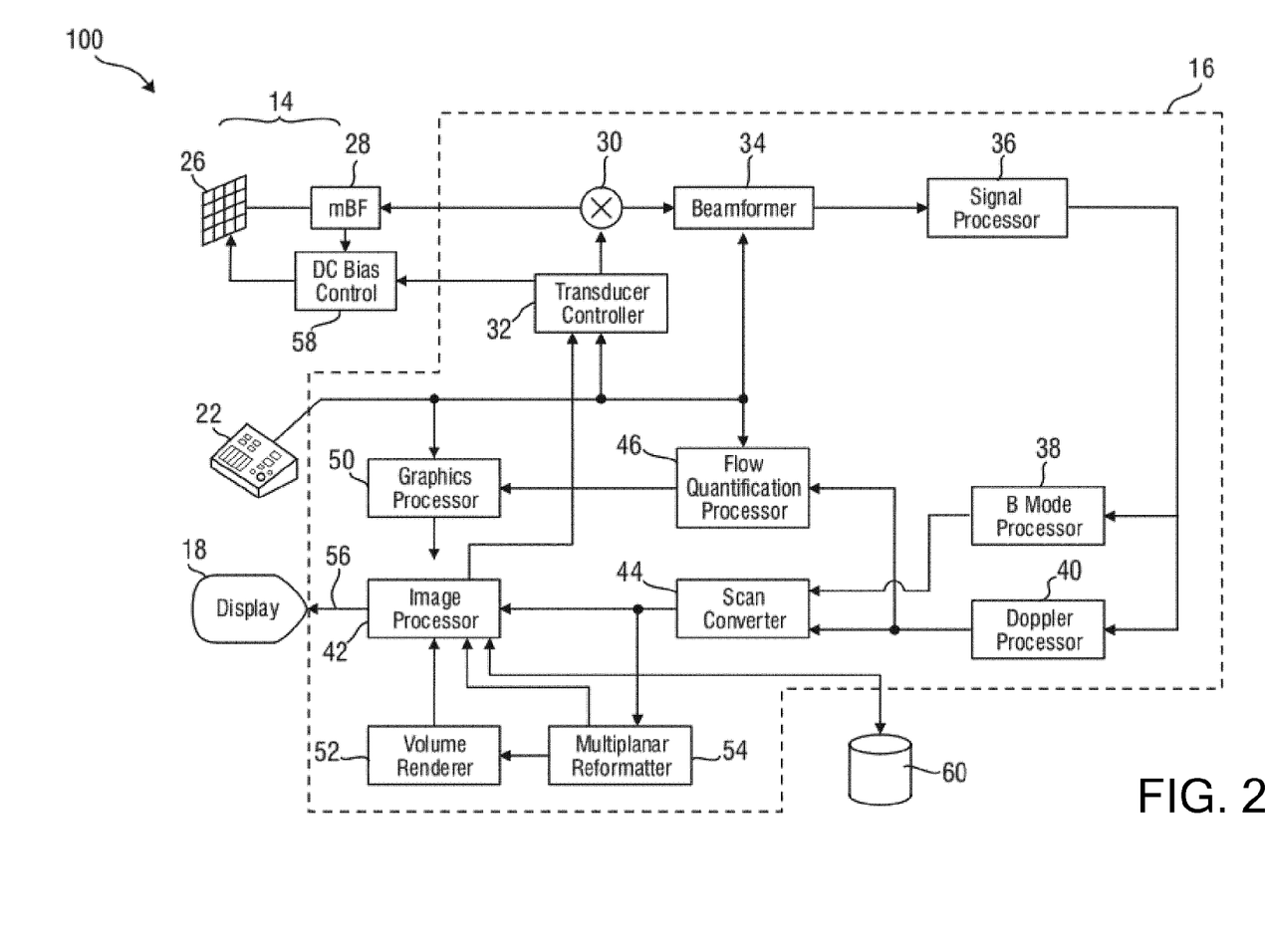
FIG. 2 schematically depicts a circuit diagram of such an ultrasound imaging system.

FIG. 2 illustrates a schematic block diagram of the ultrasound system 100 including the processor arrangement 16 of the ultrasound image processing apparatus 10. The ultrasound probe 14 may, for example, comprise a CMUT transducer array 26. The transducer array 26 may alternatively comprise piezoelectric transducer elements formed of materials such as PZT or PVDF. The transducer array 26 is a one- or a two-dimensional array of transducer elements capable of scanning in two dimensions for 2D imaging or in three dimensions for 3D imaging. The transducer array 26 is coupled to a microbeamformer 28 in the probe which controls transmission and reception of signals by the CMUT array cells or piezoelectric elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.)

The microbeamformer 28 may be coupled by a probe cable to a transmit/receive (T/R) switch 30 which switches between transmission and reception and protects the main beamformer 34 from high energy transmit signals when a microbeamformer 28 is not used and the transducer array 26 is operated directly by the main beamformer 34. The transmission of ultrasonic beams from the transducer array 26 under control of the microbeamformer 28 is directed by a transducer controller 32 coupled to the microbeamformer 28 by the T/R switch 30 and the main system beamformer 34, which receives input from the user's operation of the user interface or control panel 22. One of the functions controlled by the transducer controller 32 is the direction in which beams are steered and focused. Beams may be steered straight ahead from (orthogonal to) the transducer array 26, or at different angles for a wider field of view. The transducer controller 32 can be coupled to control a DC bias control 58 for the array of transducer cells. The DC bias control 58 sets DC bias voltage(s) that are applied to the transducer cells, e.g. CMUT cells.

The partially beamformed signals produced by the microbeamformer 26 on receive are coupled to the main beamformer 34 where partially beamformed signals from individual patches of transducer elements are combined into a fully beamformed signal. For example, the main beamformer 34 may have 128 channels, each of which receives a partially beamformed signal from a patch of dozens or hundreds of CMUT transducer cells or piezoelectric elements. In this way the signals received by thousands of transducer elements of the transducer array 26 can contribute efficiently to a single beamformed signal.

The beamformed signals are coupled to a signal processor 36, which may form part of the aforementioned processor arrangement. The signal processor 36 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and/or microbubbles comprised in a contrast agent that has been pre-administered to the body of the patient 12. The signal processor 36 may also perform additional signal enhancement such as speckle reduction, signal compounding, and noise elimination. The bandpass filter in the signal processor 36 can be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals may be transferred to a B mode processor 38 and a Doppler processor 40. The B mode processor 38 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.)

The Doppler processor 40 may process temporally distinct signals from tissue movement and blood flow for the detection of the motion of substances such as the flow of blood cells in the image field. The Doppler processor 40 typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material. This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue.

The Doppler processor 40 may receive and process a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B mode and Doppler processors 38, 40 may then be transferred to a scan converter 44 and a multiplanar reformatter 54. The scan converter 44 arranges the echo signals in the spatial relationship from which they were received in a desired image format. For instance, the scan converter 44 may arrange the echo signal into a two dimensional (2D) sector-shaped format, or a pyramidal three dimensional (3D) image. The scan converter 44 can overlay a B mode structural image with colors corresponding to motion at points in the image field with their Doppler-estimated velocities to produce a color Doppler image which depicts the motion of tissue and blood flow in the image field.

In a 3-D imaging system, the multiplanar reformatter 54 will convert echoes which are received from points in a common plane in a volumetric region of the body into an ultrasonic image of that plane, as described in U.S. Pat. No. 6,443,896 (Detmer). A volume renderer 52 converts the echo signals of a 3D data set into a projected 3D image sequence 56 over time as viewed from a given reference point as described in U.S. Pat. No. 6,530,885 (Entrekin et al.). The 3-D image sequence 56 is transferred from the scan converter 44, multiplanar reformatter 54, and volume renderer 52 to an image processor 42 for further enhancement, buffering and temporary storage for display on the display 18.

The image processor 42 for example may be adapted to map a heart model to a cardiac ultrasound image, e.g. a 2-D image or preferably a 3-D volumetric ultrasound image (or a user-selected slice thereof), and to segment the cardiac ultrasound image in accordance with any suitable segmentation algorithm, e.g. a segmentation algorithm forming part of a segmentation software module executed by the image processor 42. At this point, it should be understood that reference to the image processor 42 is intended to also cover implementations of the ultrasound image processing apparatus 10 in which the functionality of the image processor 42 is provided by a plurality of cooperating processors. For example, in such implementations, a dedicated heart model mapping processor and a dedicated segmentation processor may cooperate to implement the functionality of the image processor 42.

In addition to being used for imaging, the blood flow values produced by the Doppler processor 40 and tissue structure information produced by the B mode processor 38 may be transferred to a quantification processor 46 forming part of the processor arrangement. This quantification processor 46 may produce measures of different flow conditions such as the volume rate of blood flow as well as structural measurements such as the sizes of organs and gestational age. The quantification processor 46 may receive input from the user interface 22, such as the point in the anatomy of an image where a measurement is to be made.

Output data from the quantification processor 46 may be transferred to a graphics processor 50 forming part of the processor arrangement for the reproduction of measurement graphics and values with the image on the display 18. The graphics processor 50 can also generate graphic overlays for display with the ultrasound images, such as the overlay of the heart model 1 over a cardiac ultrasound image to which the heart model 1 is mapped. These graphic overlays can further contain standard identifying information such as patient name, date and time of the image, imaging parameters, and the like. For these purposes the graphics processor 50 may receive input from the user interface 22, such as patient name. The user interface 22 may be coupled to the transmit controller 32 to control the generation of ultrasound signals from the transducer array 26 and hence the images produced by the transducer array and the ultrasound system. The user interface 22 may also be coupled to the multiplanar reformatter 54 for selection and control of the planes of multiple multiplanar reformatted (MPR) images which may be used to perform quantified measures in the image field of the MPR images in case of a 3D imaging system.

It is reiterated that the aforementioned ultrasound system 100 has only been explained as one possible example for an application of the medical ultrasound image processing apparatus 10. It shall be noted that the aforementioned ultrasound system 100 does not have to comprise all of the components explained before. On the other hand, the ultrasound system 100 may also comprise further components, if necessary. Still further, it shall be noted that a plurality of the aforementioned components does not necessarily have to be realized as hardware, but may also be realized as software components. A plurality of the aforementioned components may also be comprised in common entities or even in one single entity and do not all have to be realized as separate entities, as this is schematically shown in FIG. 2.

Ultrasound images may be used by a clinician to derive information of diagnostic relevance from such images, such as measurements of dimensions of an anatomical body of interest within a patient, for example to ascertain whether the anatomical body is anomalous or whether the anatomical body exhibits anomalous functionality. This for example is applicable to echocardiography, in which a clinician such as a cardiologist may evaluate acquired ultrasound images of the patient's heart in order to obtain heart measurements from which the heart function can be assessed. Such measurements for example may include the volume of the entire heart or of one or more of its chambers, changes in such a volume between ultrasound images captured at different points of the cardiac cycle, e.g. to determine the ejection fraction of the heart or the heart chamber under investigation, diameter or perimeter measurements such as of the left atrial appendage, and so on. The need to obtain such measurements of an anatomical body of interest within the patient is not limited to cardiac monitoring. Similar requirements may exist for the evaluation of other organs of the patient or of a fetus in the womb of a pregnant female patient, where such measurements of particular parts of the fetus, e.g. the circumference of its head, may provide invaluable insights in anomalies in the development of the fetus.

As explained above, such anatomical measurements can be derived with a high degree of accuracy from 3-D ultrasound images in which the anatomical body of interest has been captured, for example using anatomically intelligent segmentation models that can be mapped onto the anatomical body of interest within the 3-D ultrasound image such that the anatomical measurements can be performed on a mesh defined by the segmentation model. However, this approach to obtaining such anatomical measurements may not be chosen by a clinician for a number of reasons. The clinician may not have access to 3-D ultrasound images when trying to obtain the anatomical measurements or may be reluctant to interpret such 3-D ultrasound images in a volumetric visualization mode, for example because the clinician has little experience with the evaluation of such images and may have little confidence in obtaining accurate measurement results in this manner.

Figure 3:
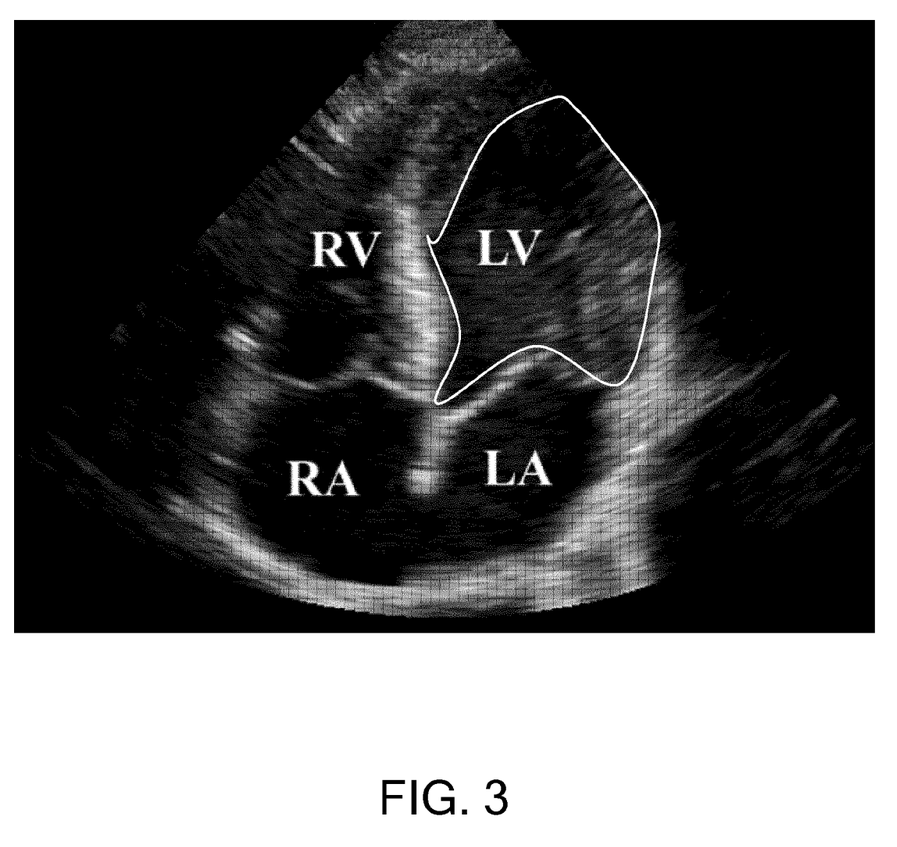
FIG. 3 is a 2-D ultrasound image of a 4-chamber view of a human heart from which a left ventricle volume is derived.

Instead, the clinician may evaluate a set of 2-D images, i.e. one or more 2-D images, of the anatomical body of interest, such as for example a four-chamber view of a cross-section of the heart of a patient as depicted in FIG. 3, in which cross-sections of the chambers of the heart (right atrium (RA), left atrium (LA), right ventricle (RV), left ventricle (LV)) delimited by their respective contours, as schematically depicted for the LV by the dashed contour, to obtain such measurements. Commonly, the clinician may rely on x-plane 2-D ultrasound images, i.e. a pair of 2-D ultrasound images of the anatomical object of interest along orthogonal viewing angles, e.g. a four-chamber view and a two-chamber view in case of cardiac ultrasound imaging, to facilitate the estimation of a 3-D measurement value of the anatomical body of interest, e.g. its volume, from such orthogonal views, as an informed assumption may be made about the overall shape and dimensions of the anatomical body of interest of the orthogonal cross-sections in such x-plane 2-D ultrasound images. The clinician typically estimates such a 3-D measurement value from 2-D measurements of the cross-sectional views of the anatomical body of interest, such as circumference (contour) length, cross-sectional area and/or largest cross-sectional measurement (diameter) using geometrical assumptions as previously explained, which can give rise to inaccuracies in the overall measurement value estimated from such 2-D measurements.

Figure 4:
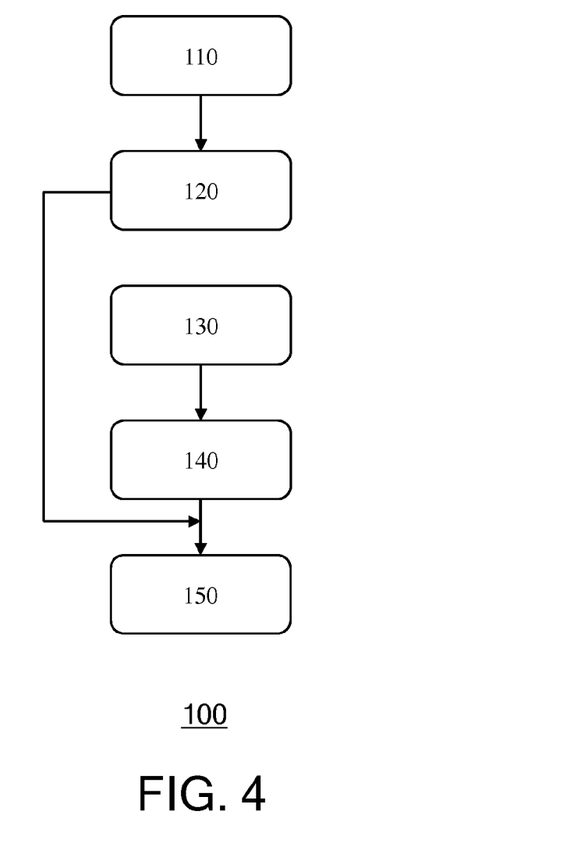
FIG. 4 is a flowchart of a computer-implemented method according to an embodiment.
Figure 5:
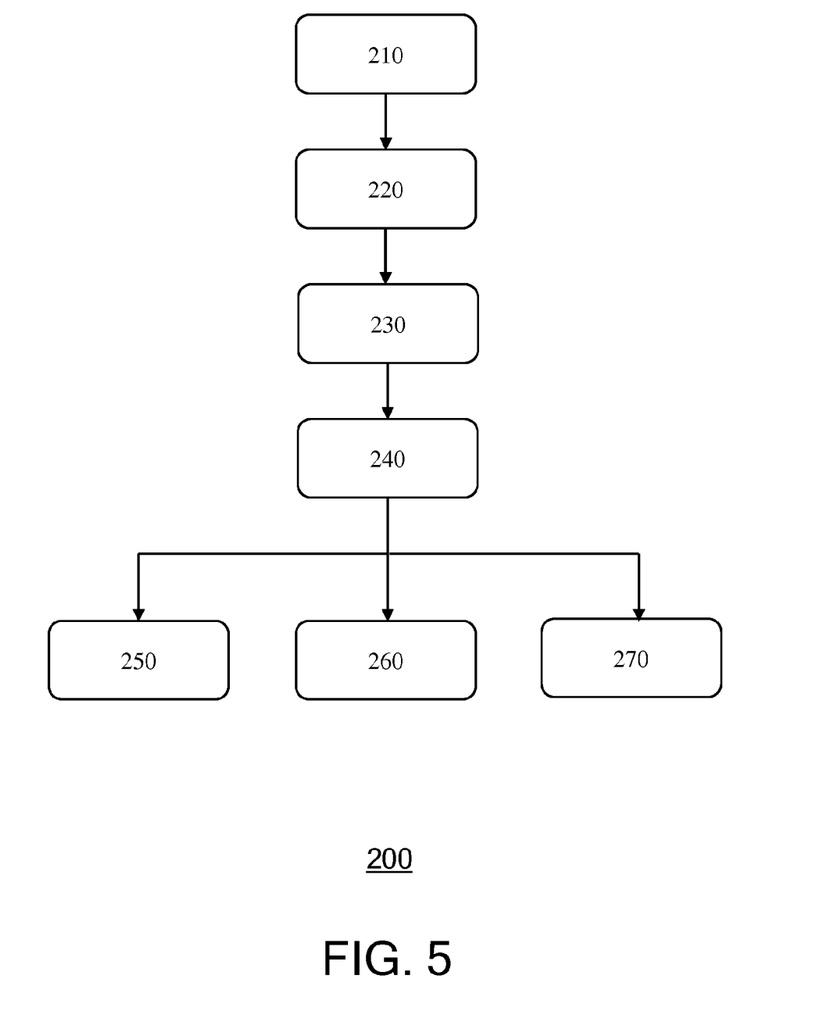
FIG. 5 is a flowchart of a computer-implemented method according to another embodiment.

In accordance with embodiments of the present invention, two interrelated methods are provided that may be executed by the processor arrangement 16 of the ultrasound image processing apparatus 10, which methods seek to assist such a clinician in obtaining measurement values of an anatomical object of interest from a set of 2-D ultrasound images such as one or more 2-D ultrasound images or at least one pair of x-plane 2-D ultrasound images without the clinician having to make such a geometrical assumptions, in order to reduce the risk that such a clinician obtains unreliable measurement values based on incorrect geometrical assumptions. A flowchart of the first method 100 is depicted in FIG. 4 and a flowchart of the second method 200 is depicted in FIG. 5. It should be understood that the ultrasound image processing apparatus 10 may be configured to implement only the first method, only the second method or both the first method and the second method.

In accordance with the first method 100, a model is developed that provides an estimator function that takes at least one 2-D ultrasound image, or at least one pair of 2-D ultrasound images, e.g. x-plane 2-D ultrasound images, as an input in which a contour or cross-section of the anatomical body of interest has been captured and that estimates the measurement value associated with the entire anatomical body of interest, e.g. a 3-D measurement value, from the at least one 2-D ultrasound image with the estimator function.

In accordance with the second method 200, such a model is executed by the processor arrangement 16 of the ultrasound image processing apparatus 10 in response to one or more received 2-D ultrasound images e.g. x-plane 2-D ultrasound images, as an input in order to provide a user of the ultrasound image processing apparatus 10 with an estimate of the anatomical body measurement value based on the received input 2-D ultrasound images in which a contour or cross-section of the anatomical body of interest has been captured.

The development of such a model with method 100 will now be explained in more detail with the aid of FIG. 4. In specific examples, reference will be made to the anatomical body of interest being a human heart but it should be understood that this is by way of non-limiting example only and that the teachings described below are equally applicable to other anatomical bodies of interest, as previously explained. In operation 110, a set of 3-D ultrasound images including the anatomical body of interest is provided. Such a set may comprise 3-D ultrasound images of different individuals such as to obtain a set of 3-D ultrasound images including different 'embodiments' of the anatomical body of interest, such as to obtain a statistically averaged set of images.

In operation 120, the ground truth values of the anatomical body measurement value of interest is derived from the set of 3-D ultrasound images including the anatomical body of interest. Such ground truth values may be obtained in any suitable manner, e.g. through manual measurement although in a preferred embodiment the ground truth values are obtained by mapping a segmentation model for identifying the anatomical body to the 3-D ultrasound image and derive the ground truth value of the anatomical body measurement from the mapped segmentation model. Such mapping may be achieved fully automatically or semi-automatically, in which case a user may manually adjust an initial mapping of the segmentation model to the 3-D ultrasound image to improve the mapping of the segmentation model to the anatomical body of interest within the 3-D ultrasound image. Upon achieving an accurate mapping of the segmentation model to the 3-D ultrasound image, the ground truth value of the anatomical body measurement can be derived by calculating it from the segmentation model, e.g. from a 3-D mesh defined by the segmentation model. The calculation of such measurement values from a segmentation model is well-known per se and is therefore not explained in further detail for the sake of brevity only.

In operation 130, which for the avoidance of doubt does not necessarily need to be performed after operation 120, a set of 2-D ultrasound image planes that each include a contour of one of the anatomical bodies in the 3-D ultrasound images provided in operation 110 is generated, such that for each anatomical body in such a 2-D ultrasound image plane a ground truth value of its anatomical measurement is available. Typically, for each 3-D ultrasound image provided in operation 110, a plurality of 2-D ultrasound image planes is provided such that measurements based on the contour or cross-section of the anatomical body in these 2-D ultrasound image planes are related to a ground truth value of an anatomical measurement of the 3-D anatomical body of interest. In a preferred embodiment, the set includes one or more pairs of orthogonal 2-D image planes (x-plane 2-D ultrasound images) in order to reflect the fact that such x-plane 2-D ultrasound images are commonly used by a clinician to estimate the anatomical body measurement value relating to the 3-D anatomical body from such 2-D ultrasound images. The 2-D ultrasound image planes may be generated independent from the 3-D ultrasound images provided in operation 110, and for example may be provided as a separate set of 2-D ultrasound images acquired in different ultrasound scans.

However, in a preferred embodiment, the set of 2-D ultrasound image planes is generated from the 3-D ultrasound images provided in operation 110. A further advantage is that in this manner different sets of 2-D ultrasound image planes can be readily generated from a single 3-D ultrasound image, e.g. image slices relating to a 4-chamber view and a 2-chamber view of a patient's heart. For example, such different 2-D ultrasound image planes may be generated based on the segmentation model mapped to a particular 3-D ultrasound image, as is well-known per se.

In this manner, for each of 3-D ultrasound image provided in operation 110, a set of 2-D ultrasound image planes may be provided in operation 130 in order to provide a large set of measurements based on cross-sections of the anatomical body of interest in these 2-D ultrasound image planes, which have a given (unknown) relationship with the ground truth value of the anatomical body measurement value of interest, such as for example a volume of the anatomical body. In a preferred embodiment, each set of 2-D ultrasound image planes comprises different subsets of 2-D ultrasound image planes, in which the 2-D ultrasound image planes in each subset are under a defined angle with a defined axis of the 3-D ultrasound image. The defined angles differ between subsets such that the different subsets reflect variations in viewing planes that may result from different users imaging the anatomical object of interest under a slightly different viewing angles.

In operation 140, for each of the 2-D image slices, or pairs of 2-D image slices, e.g. in case of x-plane images, a value of the anatomical body measurement is generated from at least one of an outline contour measurement and a cross-sectional measurement of the anatomical body in the 2-D ultrasound image plane such as the cross-section area and/or the largest dimension (diameter) of cross-section, in accordance with the usual procedures to extrapolate such an anatomical body measurement value from a 2-D image slice (or pair of such slices). This may be achieved using existing extrapolation algorithms for obtaining estimates of such anatomical body measurements. Such extrapolated values of the anatomical body measurement of interest facilitate an assessment of the accuracy of such extrapolated values, for instance by comparison of these values against the ground truth values of the anatomical body measurement of interest as obtained from the 3-D ultrasound images.

Upon completion of operation 140, a dataset has been compiled comprising the following elements: the ground truth values of the anatomical body measurement of interest extracted from each of these images, the respective sets of 2-D ultrasound image planes relating to the 3-D ultrasound images, the contour measurements performed on the 2-D ultrasound image planes such as an outline contour measurement and a cross-sectional measurement as explained above, and the values of the anatomical body measurement of interest extrapolated from these contour measurements using existing extrapolation algorithms.

This dataset is provided as inputs to a machine learning algorithm in operation 150, which machine learning algorithm is trained by this dataset in order to train an estimator function, e.g. a function $f(S_{n,1}, C_{n,1}, A_{n,1}, S_{n,2}, C_{n,2}, A_{n,2}, \ldots)$ in which S defines a set of 2-D ultrasound image planes, C defines the outline contour length of the anatomical body contour in the 2-D ultrasound image planes and A defines the cross-section area of the anatomical body contour in the 2-D ultrasound image planes to establish the relation between these input parameters and the corresponding ground truth value of the anatomical body measurement of interest, such that upon training of the machine learning algorithm, the algorithm can provide an estimate value of the anatomical body measurement based on an input including S, C and A, i.e. an input of one or more 2-D ultrasound image planes, which may be x-plane images or a sequence of 2-D ultrasound images captured or generated in any suitable manner, together with the outline contour length C of the anatomical body contour in the 2-D ultrasound image planes and the cross-section area A of the anatomical body contour in the 2-D ultrasound image planes.

In a preferred embodiment, the machine learning algorithm trains a further function $g(S_{n,1}, C_{n,1}, A_{n,1}, S_{n,2}, C_{n,2}, A_{n,2}, \ldots)$ in order to estimate an uncertainty in the estimated value of the anatomical body measurement in order to allow a user to assess the reliability of the estimated anatomical body measurement. This may be achieved in any suitable manner. For example, where the respective sets of 2-D ultrasound image planes contain subsets of 2-D ultrasound image planes sharing the same viewing angle of the anatomical body of interest (e.g. a 4-chamber view or a 2-chamber view of a human heart) for the respective 3-D ultrasound images, different subsets of such 2-D ultrasound image planes may lead to a range of differences between the estimated value and the ground truth value of the anatomical body measurement of interest, which range of differences may be determined and used to express an uncertainty in the estimation value of the anatomical body measurement of interest as obtained with the estimation function of the model as generated with the machine learning algorithm.

Such uncertainty information may be leveraged in a number of ways. For example, the presentation of such uncertainty information to a user of the ultrasound image processing apparatus 10, e.g. on the display 18 in any suitable form, may allow the user to make an assessment regarding the suitability of the 2-D ultrasound image data on which the estimation of the anatomical body measurement value is based. The user may for instance conclude that such data has been captured under a non-optimal viewing angle based on the provided uncertainty information, which may prompt the user to repeat the acquisition of the 2-D ultrasound images under a different, improved, viewing angle, e.g. under an adjusted scanning angle or trajectory of the probe 14 relative to the anatomical body of interest.

In an embodiment, the model may be further adapted to present the user with guidance as to what the optimal viewing plane of the anatomical body of interest is from which the desired measurement value can be estimated with the model with the lowest degree of uncertainty. To this end, the model may evaluate the respective degrees of uncertainty associated with different viewing planes and may communicate the optimal viewing plane to the user once this optimal viewing plane has been determined. This option may be conditionally triggered in some embodiments, for example when the determined uncertainty in the estimated value of the anatomical body measurement of interest for the actual viewing plane exceeds a predefined threshold.

Alternatively, the model may be adapted to direct such guidance information to the ultrasound probe 14. In this embodiment, the ultrasound probe 14 is responsive to such guidance information, which triggers the ultrasound probe 14 to acquire one or more 2-D ultrasound images under the identified optimal viewing plane, e.g. by electronic or mechanical steering of the ultrasound transducer elements of the probe based on the received guidance information.

At this point, it is noted that the model for estimating the anatomical body measurement value of interest as developed in accordance with the method 100 as described above may be developed on the ultrasound image processing apparatus 10 on which the model is to be implemented for use by a user of the apparatus, but this is not necessary. It is for example equally feasible that this model is developed on a separate apparatus, e.g. a computer or another ultrasound image processing apparatus adapted to develop the model, after which the developed model may be installed on the ultrasound image processing apparatus 10.

FIG. 5 is a flowchart of a method 200 of estimating an anatomical body measurement value that may be implemented by a suitably configured ultrasound image processing apparatus 10. In operation 210, the model developed in accordance with method 100 described above is installed on the processor arrangement 16 of the ultrasound image processing apparatus 10, e.g. by a user downloading and/or launching the model on the ultrasound image processing apparatus 10 through any suitable user interface of the ultrasound image processing apparatus 10, such as a monitor 18 with touchscreen functionality or the user interface 20.

In operation 220, the ultrasound image processing apparatus 10 is provided with one or more 2-D ultrasound images, which for example may have been generated using an ultrasound probe 14 for generating such 2-D ultrasound images or which may have been retrieved from the data storage arrangement 60 in which previously captured 2-D ultrasound images have been stored. The 2-D ultrasound images may be generated with a 2-D ultrasound probe 14, which may be a 3-D matrix probe to improve the resolution and frame rate of the 2-D ultrasound images, as is well known per se.

In operation 230, the contour-related measurements are derived from these images, e.g. by the user or by an algorithm such as a segmentation algorithm adapted to identify the contour of the anatomical body of interest in the 2-D ultrasound image, such as the outline contour length C of the anatomical body contour and the cross-section area A of the anatomical body contour in the 2-D ultrasound image.

In operation 240, the set S of one or more 2-D ultrasound images obtained in operation 220 and the contour-related measurements including the outline contour lengths C and the cross-section areas A for each of the 2-D ultrasound images in this set S are said to the estimation model in operation 240, based on which the estimation model estimates a value of the anatomical body measurement of interest in operation 250 using the estimation function developed by the machine learning algorithm in operation 150 of the method 100 as previously explained. Preferably, the model further estimates in operation 260 the uncertainty in the estimated value of the anatomical body measurement of interest as previously explained such that the user can assess the reliability of the accuracy of the estimated anatomical body measurement value and take appropriate action if this reliability is insufficient as previously explained. The estimated value of the anatomical body measurement of interest and optionally the associated estimated uncertainty of this value may be presented to the user in any suitable manner, such as in any suitable form on the display 18.

The model as executed by the processor arrangement 16 of the ultrasound image processing apparatus 10 may further generate the previously described guidance information regarding the 2-D ultrasound image plane orientation at which the estimated uncertainty is minimized in operation 270 either to the user or 2-D ultrasound probe 14 as previously explained in order to facilitate the acquisition of another set of 2-D ultrasound images based on which the anatomical body measurement value of interest may be estimated with a higher degree of accuracy, i.e. with a lower uncertainty.

In an embodiment, the model is further adapted to determine a dynamic change in the estimated value of the anatomical body measurement of interest, such as for example a change in this estimated value between a first set of 2-D ultrasound images of the anatomical body of interest along a defined viewing angle (or pair of orthogonal viewing angles) at a first point in time and a second set of 2-D ultrasound images of the anatomical body of interest along the same viewing angle (or pair of orthogonal viewing angles) at a second point in time. This for example is particularly applicable where the anatomical body periodically contracts and expands, such as for example is the case when the anatomical body is the heart of the patient.

In such a scenario, estimating the change of the anatomical body measurement of interest, e.g. a change in volume of the heart or a particular chamber of the heart such as the left ventricle, may be used to assess the function of the heart, for example by estimating an ejection fraction of the left ventricle (or any other part of the heart) based on the change in the estimated volume of the part of the heart being monitored at the different points in time, such as the first point in time coinciding with the end-diastolic phase and the second point in time coinciding with the end-systolic phase of the cardiac cycle.

The above described embodiments of the method 100 and/or the method 200 may be realized by computer readable program instructions embodied on a computer readable storage medium having, when executed on a processor arrangement 16, cause the processor arrangement to implement the method 100 and/or 200. Any suitable computer readable storage medium may be used for this purpose, such as for example an optically readable medium such as a CD, DVD or Blu-Ray disc, a magnetically readable medium such as a hard disk, an electronic data storage device such as a memory stick or the like, and so on. The computer readable storage medium may be a medium that is accessible over a network such as the Internet, such that the computer readable program instructions may be accessed over the network. For example, the computer readable storage medium may be a network-attached storage device, a storage area network, cloud storage or the like. The computer readable storage medium may be an Internet-accessible service from which the computer readable program instructions may be obtained. In an embodiment, the ultrasound image processing apparatus 10 is adapted to retrieve the computer readable program instructions from such a computer readable storage medium and to create a new computer readable storage medium by storing the retrieved computer readable program instructions in the data storage arrangement 60, e.g. in a memory device or the like forming part of the data storage arrangement 60.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A computer-implemented method of generating a model for estimating a 3-D anatomical body measurement value from at least one 2-D ultrasound image including a contour of the anatomical body, the method comprising:
   providing a set of 3-D ultrasound images of the anatomical body;
   for each of the 3-D ultrasound images in the set of 3-D ultrasound images, determining a ground truth value of the 3-D anatomical body measurement;
   generating from the set of 3-D ultrasound images, a set of 2-D ultrasound image planes, each including a contour of the anatomical body and, for each of the 2-D ultrasound image planes, estimating a value of the 3-D anatomical body measurement from at least one of an outline contour measurement and a cross-sectional measurement of the anatomical body in the 2-D ultrasound image plane;
   training a machine-learning algorithm by inputting to the machine-learning algorithm the ground truth values of the 3-D anatomical body measurements, the corresponding estimated values of the 3-D anatomical body measurements, and at least one of: the corresponding outline contour measurements and the corresponding cross-sectional measurements of the anatomical body in the 2-D ultrasound image planes, to generate a model for estimating a 3-D anatomical body measurement value from at least one subsequently-acquired 2-D ultrasound image comprising at least one of an outline contour measurement and a cross-sectional measurement of a contour of the anatomical body.

2. The computer-implemented method of claim 1, further comprising training the machine-learning algorithm to generate a further estimator function (g) to estimate the uncertainty in the estimated 3-D anatomical body measurement value that it generates in use, the training being done by inputting to the machine-learning algorithm the obtained ground truth values, the corresponding estimated values of the 3-D anatomical body measurement and at least one of the corresponding outline contour measurement and the corresponding cross-sectional measurement of the anatomical body in the 2-D ultrasound image planes.

3. The computer-implemented method of claim 1, wherein determining a ground truth value of the 3-D anatomical body measurement comprises:
   mapping a segmentation model of the anatomical body to said anatomical body within the 3-D ultrasound image; and
   determining the ground truth value of the 3-D anatomical body measurement from the mapped segmentation model.

4. The computer-implemented method of claim 3, wherein generating the set of 2-D image planes from the 3-D ultrasound image comprises generating the set of 2-D image planes from the 3-D ultrasound image based on the segmentation model that has been mapped to the anatomical body within the 3-D ultrasound image.

5. The computer-implemented method of claim 3, wherein the anatomical body is a human heart and the segmentation model is a heart model.

6. The computer-implemented method of claim 1, wherein generating the set of 2-D image planes comprises providing a first set of 2-D image slices providing a 2-chamber view of a human heart and a second set of 2-D image slices providing a 4-chamber view of the human heart.

7. The computer-implemented method of claim 1, wherein generating the set of 2-D ultrasound image planes comprises providing a plurality of subsets of 2-D ultrasound image planes, wherein the 2-D ultrasound image planes in each subset are under a defined angle with a defined axis of the 3-D ultrasound images, said defined angles differing between subsets.

8. A computer-implemented method of estimating a 3-D anatomical body measurement value from at least one 2-D ultrasound image including a contour of the anatomical body using the model obtained by the computer-implemented method of any preceding claim, comprising:
   providing the at least one 2-D ultrasound image including a contour of the anatomical body;
   determining at least one of an outline contour measurement and a cross-sectional measurement of the anatomical body from the at least one 2-D ultrasound image;
   providing at least one of the determined outline contour measurement and the determined cross-sectional measurement as an input to said model;
   receiving an estimated 3-D anatomical body measurement value from the model in response to said input; and
   receiving an estimated uncertainty in the value of the estimated 3-D anatomical body measurement value from the model in response to said input.

9. The computer-implemented method of claim 8, further comprising identifying a plane orientation of the at least one 2-D ultrasound image relative to the anatomical body for which said estimated uncertainty is minimized and communicating said plane orientation to a user or to an ultrasound probe.

10. The computer-implemented method of claim 8, wherein the anatomical body is the human heart and the estimated 3-D measurement value is a volume of at least a part of the human heart, and wherein providing the at least one 2-D ultrasound image including a contour of the anatomical body comprises:
   providing a first 2-D ultrasound image including a contour of the human heart at a first point of a cardiac cycle;

providing a second 2-D ultrasound image including a contour of the human heart at a second point of a cardiac cycle; and deriving an estimation of an ejection fraction of the human heart from a difference between the estimated volume for the first 2-D ultrasound image and the estimated volume for the second 2-D ultrasound image.

11. A non-transitory computer readable storage medium comprising computer readable program instructions embodied therewith for, when executed on a processor arrangement of an ultrasound image processing apparatus, causing the processor arrangement to implement the method of claim 1.

12. A non-transitory computer readable storage medium comprising computer readable program instructions embodied therewith for, when executed on a processor arrangement of an ultrasound image processing apparatus, causing the processor arrangement to implement the method of claim 8.

* * * * *